United States Patent
Ngo-Chu et al.

(10) Patent No.: US 11,471,650 B2
(45) Date of Patent: Oct. 18, 2022

(54) MECHANISM FOR MANIPULATING A PULLER WIRE

(71) Applicant: BIOSENSE WEBSTER (ISRAEL) LTD., Yokneam (IL)

(72) Inventors: Don Q. Ngo-Chu, Los Angeles, CA (US); Susan Ayer, Duarte, CA (US); Christopher T. Beeckler, Brea, CA (US); Kevin J. Herrera, West Covina, CA (US); Joseph T. Keyes, Sierra Madre, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 111 days.

(21) Appl. No.: 17/012,042

(22) Filed: Sep. 3, 2020

(65) Prior Publication Data

US 2021/0085925 A1   Mar. 25, 2021

Related U.S. Application Data

(60) Provisional application No. 62/903,560, filed on Sep. 20, 2019.

(51) Int. Cl.
*A61M 25/01* (2006.01)
*A61M 25/09* (2006.01)
*A61M 1/00* (2006.01)

(52) U.S. Cl.
CPC .......... *A61M 25/0147* (2013.01); *A61M 1/85* (2021.05); *A61M 25/0136* (2013.01); *A61M 25/09* (2013.01); *A61M 2205/02* (2013.01)

(58) Field of Classification Search
CPC .......... A61M 25/0147; A61M 25/0136; A61M 25/09; A61M 25/0105; A61M 1/85; A61M 2205/02
See application file for complete search history.

(56) References Cited

U.S. PATENT DOCUMENTS 3,109,461 A   11/1963   Wolff et al.
3,757,768 A   9/1973   Kline
(Continued)

FOREIGN PATENT DOCUMENTS

AU   2007285898 B2 *   7/2013   ......... A61B 17/0469
CA   2622742 A1   3/2007
(Continued)

OTHER PUBLICATIONS

Australian Patent Office Examination Report No. 1 for Application No. 2013205935, dated Feb. 28, 2017, 4 pages.
(Continued)

*Primary Examiner* — Emily L Schmidt
*Assistant Examiner* — Adam J. Cermak
(74) *Attorney, Agent, or Firm* — Etan S. Chatlynne; Calderon Safran & Cole P.C.

(57) ABSTRACT

A catheter that includes a mechanism for deflecting a distal portion of a catheter may include a deflection knob including a first thread, a rod including a second thread that is coupled to the first thread, and a puller wire that is connected to the rod. The rod may additionally include a pocket to which the puller wire may be connected via a joining feature that may be secured in the pocket and attached to a proximal end of the puller wire. The joining feature may include a first ferrule joined, e.g., crimped, to the proximal end of the puller wire and a second ferrule secured, e.g., bonded, in the pocket and joined, e.g., crimped, to the first ferrule.

17 Claims, 6 Drawing Sheets

(56) References Cited

U.S. PATENT DOCUMENTS

| | | |
|---|---|---|
| 4,203,430 A | 5/1980 | Takahashi |
| 4,353,358 A | 10/1982 | Emerson |
| 4,742,817 A | 5/1988 | Kawashima et al. |
| 4,753,223 A | 6/1988 | Bremer |
| 4,886,067 A | 12/1989 | Palermo |
| 4,911,148 A | 3/1990 | Sosnowski et al. |
| 4,930,494 A | 6/1990 | Takehana et al. |
| 4,963,699 A | 10/1990 | Urushibata et al. |
| 5,203,772 A | 4/1993 | Hammerslag et al. |
| 5,228,441 A | 7/1993 | Lundquist |
| 5,273,535 A | 12/1993 | Edwards et al. |
| RE34,502 E | 1/1994 | Webster, Jr. |
| 5,281,217 A | 1/1994 | Edwards et al. |
| 5,304,131 A | 4/1994 | Paskar |
| 5,315,996 A | 5/1994 | Lundquist |
| 5,322,064 A | 6/1994 | Lundquist |
| 5,325,845 A | 7/1994 | Adair |
| 5,334,145 A | 8/1994 | Lundquist et al. |
| 5,357,979 A | 10/1994 | Imran |
| 5,358,479 A | 10/1994 | Wilson |
| 5,364,352 A | 11/1994 | Cimino et al. |
| 5,381,782 A | 1/1995 | Delarama et al. |
| 5,383,852 A | 1/1995 | Stevens-Wright |
| 5,391,147 A | 2/1995 | Imran et al. |
| 5,391,199 A | 2/1995 | Ben-Haim |
| 5,401,258 A | 3/1995 | Voda |
| 5,437,288 A | 8/1995 | Schwartz et al. |
| 5,441,483 A | 8/1995 | Avitall |
| 5,443,489 A | 8/1995 | Ben-Haim |
| 5,462,527 A | 10/1995 | Stevens-Wright et al. |
| 5,467,763 A | 11/1995 | McMahon et al. |
| 5,477,856 A | 12/1995 | Lundquist |
| 5,480,382 A | 1/1996 | Hammerslag et al. |
| 5,480,422 A | 1/1996 | Ben-Haim |
| 5,517,989 A | 5/1996 | Frisbie et al. |
| 5,542,434 A | 8/1996 | Imran et al. |
| 5,546,951 A | 8/1996 | Ben-Haim |
| 5,558,091 A | 9/1996 | Acker et al. |
| 5,562,619 A | 10/1996 | Mirarchi et al. |
| 5,617,854 A | 4/1997 | Munsif |
| 5,626,136 A | 5/1997 | Webster, Jr. |
| 5,642,736 A | 7/1997 | Witall |
| 5,643,255 A | 7/1997 | Organ |
| 5,646,938 A | 7/1997 | Wagener |
| 5,658,623 A | 8/1997 | Batawi et al. |
| 5,702,433 A | 12/1997 | Taylor et al. |
| 5,782,239 A | 7/1998 | Webster, Jr. |
| 5,782,828 A | 7/1998 | Chen et al. |
| 5,807,249 A | 9/1998 | Qin et al. |
| 5,823,955 A | 10/1998 | Kuck et al. |
| 5,827,278 A | 10/1998 | Webster, Jr. |
| 5,843,152 A | 12/1998 | Tu et al. |
| 5,849,011 A | 12/1998 | Jones et al. |
| 5,861,024 A | 1/1999 | Rashidi |
| 5,891,088 A | 4/1999 | Thompson et al. |
| 5,897,529 A | 4/1999 | Ponzi |
| 5,911,715 A | 6/1999 | Berg et al. |
| 5,911,720 A | 6/1999 | Bourne et al. |
| 5,919,199 A | 7/1999 | Kelly et al. |
| 5,931,811 A | 8/1999 | Haissaguerre et al. |
| 5,935,102 A | 8/1999 | Bowden et al. |
| 5,938,616 A | 8/1999 | Eaton et al. |
| 5,961,513 A | 10/1999 | Swanson et al. |
| 5,964,757 A | 10/1999 | Ponzi |
| 5,971,975 A | 10/1999 | Mills et al. |
| 5,984,907 A | 11/1999 | McGee et al. |
| 6,002,955 A | 12/1999 | Willems et al. |
| 6,012,494 A | 1/2000 | Balazs |
| 6,027,863 A | 2/2000 | Donadio, III |
| 6,033,378 A | 3/2000 | Lundquist et al. |
| 6,048,339 A | 4/2000 | Zirps et al. |
| 6,059,769 A | 5/2000 | Lunn et al. |
| 6,102,886 A | 8/2000 | Lundquist et al. |
| 6,119,041 A | 9/2000 | Pomeranz et al. |
| 6,120,476 A * | 9/2000 | Fung ............... A61M 25/0136 604/95.04 |
| 6,123,699 A | 9/2000 | Webster, Jr. |
| 6,146,381 A | 11/2000 | Bowe et al. |
| 6,152,911 A | 11/2000 | Giannoble |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,210,407 B1 | 4/2001 | Webster |
| 6,210,409 B1 | 4/2001 | Ellman et al. |
| 6,226,542 B1 | 5/2001 | Reisfeld |
| 6,254,588 B1 | 7/2001 | Jones et al. |
| 6,267,746 B1 | 7/2001 | Bumbalough |
| 6,287,301 B1 | 9/2001 | Thompson et al. |
| 6,292,695 B1 | 9/2001 | Webster, Jr. et al. |
| 6,301,496 B1 | 10/2001 | Reisfeld |
| 6,332,881 B1 | 12/2001 | Garner et al. |
| 6,338,725 B1 | 1/2002 | Hermann et al. |
| 6,371,955 B1 | 4/2002 | Fuimaono et al. |
| 6,428,489 B1 | 8/2002 | Jacobsen et al. |
| 6,458,123 B1 | 10/2002 | Brucker et al. |
| 6,485,455 B1 | 11/2002 | Thompson et al. |
| 6,491,626 B1 | 12/2002 | Stone et al. |
| 6,500,167 B1 | 12/2002 | Webster, Jr. |
| 6,522,930 B1 | 2/2003 | Schaer et al. |
| 6,522,933 B2 | 2/2003 | Nguyen |
| 6,530,913 B1 | 3/2003 | Giba et al. |
| 6,533,770 B1 | 3/2003 | Lepulu et al. |
| 6,547,757 B1 | 4/2003 | Kranz et al. |
| 6,551,302 B1 | 4/2003 | Rosinko et al. |
| 6,554,794 B1 | 4/2003 | Mueller et al. |
| 6,585,717 B1 | 7/2003 | Wittenberger et al. |
| 6,585,718 B2 | 7/2003 | Hayzelden et al. |
| 6,591,472 B1 | 7/2003 | Noone et al. |
| 6,610,058 B2 | 8/2003 | Flores |
| 6,628,976 B1 | 9/2003 | Fuimaono et al. |
| 6,647,281 B2 | 11/2003 | Morency |
| 6,690,963 B2 | 2/2004 | Ben-Haim et al. |
| 6,699,241 B2 | 3/2004 | Rappaport et al. |
| 6,733,499 B2 | 5/2004 | Scheib |
| 6,795,721 B2 | 9/2004 | Coleman et al. |
| 6,814,733 B2 | 11/2004 | Schwartz et al. |
| 6,817,999 B2 | 11/2004 | Berube et al. |
| 6,858,024 B1 | 2/2005 | Berg et al. |
| 6,866,662 B2 | 3/2005 | Fuimaono et al. |
| 6,890,329 B2 | 5/2005 | Carroll et al. |
| 6,892,091 B1 | 5/2005 | Ben-Haim et al. |
| 6,893,436 B2 | 5/2005 | Woodard et al. |
| 6,913,604 B2 | 7/2005 | Mihalik et al. |
| 6,922,579 B2 | 7/2005 | Taimisto et al. |
| 6,926,711 B2 | 8/2005 | Lentz et al. |
| 6,997,924 B2 | 2/2006 | Schwartz et al. |
| 7,008,375 B2 | 3/2006 | Weisel |
| 7,008,401 B2 | 3/2006 | Thompson et al. |
| 7,011,655 B2 | 3/2006 | Thompson et al. |
| 7,025,759 B2 | 4/2006 | Muller |
| 7,048,711 B2 | 5/2006 | Rosenman et al. |
| 7,099,717 B2 | 8/2006 | Woodard et al. |
| 7,141,024 B2 | 11/2006 | Gaber |
| 7,156,816 B2 | 1/2007 | Schwartz et al. |
| 7,187,963 B2 | 3/2007 | Coleman et al. |
| 7,232,422 B2 | 6/2007 | Gibson et al. |
| 7,269,453 B2 | 9/2007 | Mogul |
| 7,374,553 B2 | 5/2008 | Koerner et al. |
| 7,377,906 B2 | 5/2008 | Selkee |
| 7,435,240 B2 | 10/2008 | Barkhahn et al. |
| 7,465,288 B2 | 12/2008 | Dudney et al. |
| 7,536,218 B2 | 5/2009 | Govari et al. |
| 7,588,555 B2 | 9/2009 | Pudelko et al. |
| 7,591,799 B2 | 9/2009 | Selkee |
| 7,594,903 B2 | 9/2009 | Webler et al. |
| 7,613,497 B2 | 11/2009 | Govari et al. |
| 7,623,899 B2 | 11/2009 | Worley et al. |
| 7,682,358 B2 | 3/2010 | Gullickson et al. |
| 7,756,576 B2 | 7/2010 | Levin |
| 7,803,130 B2 | 9/2010 | Ryan et al. |
| 7,815,637 B2 | 10/2010 | Ormsby et al. |
| 7,914,440 B2 | 3/2011 | Otawara |

(56) References Cited

U.S. PATENT DOCUMENTS

| | | | |
|---|---|---|---|
| 3,007,463 A1 | 8/2011 | Pudelko et al. | |
| 7,996,085 B2 | 8/2011 | Levin | |
| 8,348,888 B2 | 1/2013 | Selkee | |
| 8,406,875 B2 | 3/2013 | Levin et al. | |
| 8,556,850 B2 * | 10/2013 | Tegg | A61M 25/0136 604/95.04 |
| 9,033,916 B2 * | 5/2015 | Schultz | A61B 5/6857 606/41 |
| 9,050,010 B2 | 6/2015 | Bui et al. | |
| 9,131,953 B2 | 9/2015 | Baur et al. | |
| 9,326,818 B2 | 5/2016 | Bui et al. | |
| 9,433,752 B2 | 9/2016 | Jimenez et al. | |
| 9,629,982 B2 | 4/2017 | Caples et al. | |
| 9,694,161 B2 | 7/2017 | Selkee | |
| 9,849,268 B2 | 12/2017 | Jimenez | |
| 9,918,791 B2 | 3/2018 | Bui et al. | |
| 9,974,927 B2 | 5/2018 | Jimenez et al. | |
| 10,463,834 B2 | 11/2019 | Caples et al. | |
| 10,485,610 B2 | 11/2019 | Bui et al. | |
| 10,639,099 B2 | 5/2020 | Garcia et al. | |
| 2001/0025134 A1 | 9/2001 | Bon et al. | |
| 2001/0041891 A1 | 11/2001 | Thompson et al. | |
| 2002/0068868 A1 | 6/2002 | Thompson et al. | |
| 2002/0082585 A1 | 6/2002 | Carroll et al. | |
| 2002/0116038 A1 | 8/2002 | Muuranto et al. | |
| 2002/0120253 A1 | 8/2002 | Ouchi | |
| 2002/0143378 A1 | 10/2002 | Nguyen | |
| 2002/0162683 A1 | 11/2002 | Fujiwara | |
| 2002/0165441 A1 | 11/2002 | Coleman et al. | |
| 2002/0165461 A1 | 11/2002 | Hayzelden et al. | |
| 2003/0009208 A1 | 1/2003 | Snyder et al. | |
| 2003/0105453 A1 | 6/2003 | Stewart et al. | |
| 2003/0120195 A1 | 6/2003 | Milo et al. | |
| 2003/0125720 A1 | 7/2003 | Woodard et al. | |
| 2003/0181855 A1 | 9/2003 | Simpson et al. | |
| 2004/0116849 A1 | 6/2004 | Gardeski | |
| 2004/0181136 A1 | 9/2004 | McDaniel et al. | |
| 2004/0199051 A1 | 10/2004 | Weisel | |
| 2004/0230178 A1 | 11/2004 | Wu | |
| 2004/0243102 A1 | 12/2004 | Berg et al. | |
| 2005/0015082 A1 | 1/2005 | O'Sullivan et al. | |
| 2005/0015083 A1 * | 1/2005 | Koblish | A61N 1/056 606/41 |
| 2005/0070844 A1 | 3/2005 | Chow et al. | |
| 2005/0096590 A1 | 5/2005 | Gullickson et al. | |
| 2005/0107737 A1 | 5/2005 | McDaniel | |
| 2005/0228274 A1 | 10/2005 | Boese et al. | |
| 2005/0256452 A1 | 11/2005 | DeMarchi et al. | |
| 2005/0267459 A1 | 12/2005 | Belhe et al. | |
| 2005/0273085 A1 | 12/2005 | Hinman et al. | |
| 2005/0277875 A1 | 12/2005 | Selkee | |
| 2006/0074297 A1 | 4/2006 | Viswanathan | |
| 2006/0095030 A1 | 5/2006 | Avitall et al. | |
| 2006/0100640 A1 * | 5/2006 | Bolduc | A61B 17/00234 606/108 |
| 2006/0184106 A1 | 8/2006 | McDaniel et al. | |
| 2006/0189896 A1 | 8/2006 | Davis et al. | |
| 2006/0252984 A1 * | 11/2006 | Rahdert | A61B 17/0401 623/2.37 |
| 2006/0252993 A1 | 11/2006 | Freed et al. | |
| 2007/0066878 A1 | 3/2007 | Worley et al. | |
| 2007/0156114 A1 | 7/2007 | Worley et al. | |
| 2007/0156133 A1 * | 7/2007 | McDaniel | A61B 18/1492 604/95.04 |
| 2007/0208252 A1 | 9/2007 | Makower | |
| 2007/0233044 A1 | 10/2007 | Wallace et al. | |
| 2008/0045976 A1 * | 2/2008 | Gibbons | A61B 17/0469 606/139 |
| 2008/0103520 A1 | 5/2008 | Selkee | |
| 2008/0127704 A1 | 6/2008 | Yamanaka et al. | |
| 2008/0211728 A1 | 9/2008 | Eray | |
| 2008/0255540 A1 | 10/2008 | Selkee | |
| 2008/0300462 A1 | 12/2008 | Intoccia et al. | |
| 2009/0018497 A1 | 1/2009 | Birchard et al. | |
| 2009/0018562 A1 * | 1/2009 | Amplatz | A61B 17/0057 606/191 |
| 2009/0036833 A1 | 2/2009 | Parins | |
| 2009/0141683 A1 | 6/2009 | Grinshpun et al. | |
| 2009/0171187 A1 | 7/2009 | Gerhart et al. | |
| 2009/0234280 A1 | 9/2009 | Tah et al. | |
| 2009/0281524 A1 * | 11/2009 | Scheibe | A61M 25/0136 604/528 |
| 2009/0306653 A1 | 12/2009 | Anderson | |
| 2009/0312756 A1 | 12/2009 | Schlesinger et al. | |
| 2010/0004591 A1 | 1/2010 | Barenboym et al. | |
| 2010/0004633 A1 | 1/2010 | Rothe et al. | |
| 2010/0069834 A1 * | 3/2010 | Schultz | A61M 25/0147 604/95.04 |
| 2010/0152731 A1 | 6/2010 | De La Rama et al. | |
| 2010/0168548 A1 | 7/2010 | Govari et al. | |
| 2010/0168666 A1 | 7/2010 | Tegg | |
| 2010/0168827 A1 | 7/2010 | Schultz | |
| 2010/0222859 A1 | 9/2010 | Govari et al. | |
| 2011/0004157 A1 | 1/2011 | Dewaele et al. | |
| 2011/0054287 A1 | 3/2011 | Schultz | |
| 2011/0102395 A1 | 5/2011 | Cheng et al. | |
| 2011/0144576 A1 | 6/2011 | Rothe et al. | |
| 2011/0152880 A1 | 6/2011 | Alvarez et al. | |
| 2011/0264089 A1 | 10/2011 | Zirkle et al. | |
| 2011/0270172 A1 | 11/2011 | Selkee | |
| 2011/0282176 A1 * | 11/2011 | Tegg | A61M 25/0147 604/95.04 |
| 2012/0116200 A1 | 5/2012 | Roy et al. | |
| 2012/0123327 A1 | 5/2012 | Miller | |
| 2012/0130173 A1 | 5/2012 | Lutze et al. | |
| 2012/0157915 A1 | 6/2012 | Hastings et al. | |
| 2012/0172703 A1 | 7/2012 | Esguerra et al. | |
| 2012/0195078 A1 | 8/2012 | Levin et al. | |
| 2013/0006238 A1 | 1/2013 | Ditter et al. | |
| 2013/0018306 A1 | 1/2013 | Ludwin | |
| 2013/0085492 A1 | 4/2013 | Plascencia, Jr. et al. | |
| 2013/0184642 A1 * | 7/2013 | O'Donnell | A61M 25/0147 604/95.04 |
| 2013/0231657 A1 | 9/2013 | Datta et al. | |
| 2013/0253505 A1 | 9/2013 | Schultz | |
| 2013/0317375 A1 | 11/2013 | Garcia et al. | |
| 2014/0194753 A1 | 7/2014 | Dekker et al. | |
| 2014/0221920 A1 * | 8/2014 | Jimenez | A61M 25/0147 604/95.04 |
| 2014/0343434 A1 | 11/2014 | Elbert | |
| 2015/0088115 A1 | 3/2015 | Smith | |
| 2016/0058975 A1 * | 3/2016 | Kimmel | A61M 25/0147 600/411 |
| 2016/0144153 A1 * | 5/2016 | Selkee | A61M 25/0141 604/95.04 |
| 2016/0331932 A1 * | 11/2016 | Davies | A61M 25/0136 |
| 2017/0100582 A1 * | 4/2017 | McEvoy | A61N 1/0573 |
| 2017/0143413 A1 | 5/2017 | Levin et al. | |
| 2018/0055562 A1 * | 3/2018 | Aujla | A61B 17/00234 |
| 2018/0207404 A1 | 7/2018 | Worley et al. | |
| 2018/0221624 A1 | 8/2018 | Ludwin et al. | |
| 2018/0272108 A1 * | 9/2018 | Padilla | A61M 25/005 |
| 2020/0061341 A1 | 2/2020 | Caples et al. | |
| 2020/0093540 A1 | 3/2020 | Bui et al. | |
| 2020/0163694 A1 * | 5/2020 | Lenker | A61M 29/00 |
| 2021/0016056 A1 * | 1/2021 | Drake | A61N 1/3756 |
| 2021/0016063 A1 * | 1/2021 | Drake | A61M 25/0147 |
| 2021/0138195 A1 * | 5/2021 | Blumenkranz | A61B 34/71 |
| 2021/0316112 A1 * | 10/2021 | Zhang | A61M 25/0136 |
| 2021/0378648 A1 * | 12/2021 | Thissen | A61B 17/00234 |

FOREIGN PATENT DOCUMENTS

| | | |
|---|---|---|
| CN | 1093933 A | 10/1994 |
| CN | 101415362 A | 4/2009 |
| CN | 101584905 A | 11/2009 |
| CN | 101766502 A | 7/2010 |
| CN | 101896217 A | 11/2010 |
| CN | 102000379 A | 4/2011 |
| CN | 102159278 A | 8/2011 |
| CN | 102232869 A | 11/2011 |
| CN | 103648573 B | 11/2015 |

(56) References Cited

FOREIGN PATENT DOCUMENTS

| | | |
|---|---|---|
| EP | 0521595 A2 | 1/1993 |
| EP | 0605796 A2 | 7/1994 |
| EP | 0928601 A1 | 7/1999 |
| EP | 0937481 A1 | 8/1999 |
| EP | 0980693 A1 | 2/2000 |
| EP | 1072281 A1 | 1/2001 |
| EP | 0980693 B1 | 1/2005 |
| EP | 1532999 A2 | 5/2005 |
| EP | 1690564 A1 | 8/2006 |
| EP | 2165730 A1 | 3/2010 |
| EP | 2172240 A1 | 4/2010 |
| EP | 2289592 A2 | 3/2011 |
| EP | 2305115 A1 | 4/2011 |
| EP | 2380518 A2 | 10/2011 |
| EP | 2289592 B1 | 10/2012 |
| EP | 2587275 A1 | 5/2013 |
| EP | 2707076 B1 | 11/2018 |
| FR | 2368256 A1 | 5/1978 |
| JP | H05163 U | 1/1993 |
| JP | H05115426 A | 5/1993 |
| JP | H06292728 A | 10/1994 |
| JP | H07505554 A | 6/1995 |
| JP | H07255855 A | 10/1995 |
| JP | H10137340 A | 5/1998 |
| JP | H10290806 A | 11/1998 |
| JP | H11401 A | 1/1999 |
| JP | 2000102621 A | 4/2000 |
| JP | 2000288095 A | 10/2000 |
| JP | 2002508227 A | 3/2002 |
| JP | 2003319915 A | 11/2003 |
| JP | 2004533892 A | 11/2004 |
| JP | 2006015018 A | 1/2006 |
| JP | 2006255401 A | 9/2006 |
| JP | 2007181689 A | 7/2007 |
| JP | 2008190910 A | 8/2008 |
| JP | 2008245766 A | 10/2008 |
| JP | 2009512497 A | 3/2009 |
| JP | 2009527344 A | 7/2009 |
| JP | 2009530051 A | 8/2009 |
| JP | 2009537280 A | 10/2009 |
| JP | 2010500888 A | 1/2010 |
| JP | 2010075530 A | 4/2010 |
| JP | 2010253125 A | 11/2010 |
| JP | 2011505747 A | 2/2011 |
| JP | 2011045720 A | 3/2011 |
| JP | 2011224373 A | 11/2011 |
| JP | 2011229920 A | 11/2011 |
| JP | 2012100829 A | 5/2012 |
| JP | 2012510831 A | 5/2012 |
| JP | 5115426 B2 | 1/2013 |
| JP | 7043310 B2 * | 3/2022 ......... A61B 18/1492 |
| RU | 2006118345 A | 12/2007 |
| WO | 9308869 A1 | 5/1993 |
| WO | 9417856 A1 | 8/1994 |
| WO | 9605758 A1 | 2/1996 |
| WO | 2005048858 A1 | 6/2005 |
| WO | 2005094665 A2 | 10/2005 |
| WO | 2005094665 A3 | 12/2005 |
| WO | 2006135774 A1 | 12/2006 |
| WO | 2007035554 A1 | 3/2007 |
| WO | 2007082216 A1 | 7/2007 |
| WO | 2010035599 A1 | 4/2010 |
| WO | 2010063078 A1 | 6/2010 |
| WO | 2010136275 A1 | 12/2010 |
| WO | 2010148088 A2 | 12/2010 |
| WO | 2011046874 A1 | 4/2011 |
| WO | 2012019229 A1 | 2/2012 |
| WO | 2015000500 A1 | 1/2015 |
| WO | 2015092768 A1 | 6/2015 |
| WO | WO-2018116162 A1 * | 6/2018 ......... A61B 1/00039 |

OTHER PUBLICATIONS

CIPO Office Action for Canadian Application No. 2635676, dated Jan. 16, 2015, 4 pages(Examiner's Requisition).
CIPO Office Action for Canadian Application No. 2635676, dated Dec. 19, 2013, 3 pages.
Co-pending U.S. Appl. No. 16/866,026, filed May 4, 2020.
English translation of Japanese Patent Office action for Japanese Application No. 2008-548808, dated Oct. 23, 2012, 2 pages.
European Patent Office Communication dated Apr. 14, 2014 and Extended European Search Report for European Patent No. 14153915, 9 pages.
European Search Report for European Application No. 04251137.8, dated Jul. 5, 2004, 3 pages.
European Search Report for European Application No. 06840297.3-2305, dated Jan. 4, 2013, 9 pages.
Extended European Search Report for European Application No. 12176163, dated Nov. 20, 2012, 9 pages.
Extended European Search Report for European Application No. 12199721.7, dated Jul. 25, 2013, 10 pages.
Extended European Search Report for European Application No. 13160787.1, dated Jul. 16, 2013, 12 pages.
Extended European Search Report for European Application No. 13169246.9, dated Sep. 17, 2013, 6 pages.
Extended European Search Report for European Application No. 13192763.4, dated Feb. 6, 2014, 9 pages.
Extended European Search Report for European Application No. 13199532.6, dated Apr. 3, 2014, 6 pages.
Extended European Search Report for European Application No. EP16200173, dated Apr. 11, 2017, 9 pages.
Heart Rhythm, May Supplement 2005, vol. 2(5), pp. S154-S155.
International Search Report and Written Opinion for International Application No. PCT/US2006/62215, dated Oct. 4, 2007, 5 pages.
Japanese Notification of Reasons for Refusal issued in Japanese Application No. 2013-061576, dated Dec. 20, 2016, 11 pages (with English Language Translation).
Office Action for Chinese Application No. 201210579799.5, dated Dec. 28, 2015, 11 pages (with English Translation).
Office Action for Chinese Application No. 201310196351, dated Apr. 5, 2017, 12 pages.
Office Action for Chinese Application No. 201310196351, dated Jun. 2, 2016, 9 pages.
Office Action for European Application No. 06840297.3 -1652, dated Jan. 24, 2014, 9 pages.
Office Action for European Application No. 13192776, dated Feb. 19, 2014, 8 pages.
Office Action for Japanese Application No. 2013-109703, dated Oct. 25, 2016, 4 pages.
Partial European Search Report for European Application No. 12199721.7, dated Apr. 3, 2013, 5 pages.
SIPO Search Report for Chinese Application No. 201210579799.5, dated Dec. 17, 2015, 2 pages.
Extended European Search Report for European Application No. EP20197045.6, dated Feb. 22, 2021, 8 pages.

* cited by examiner

MECHANISM FOR MANIPULATING A PULLER WIRE

CROSS-REFERENCE TO CO-PENDING APPLICATION

The present application claims priority under 35 U.S.C. § 119 to U.S. Provisional Patent Application No. 62/903,560, filed Sep. 20, 2019. The entire contents of this application is incorporated by reference herein in its entirety.

FIELD

The subject matter disclosed herein relates to a mechanism for deflecting a distal portion of a catheter.

BACKGROUND

Catheter-deflection technology and improvements thereto, such as ergonomic improvements, remain an ongoing concern in the medical arts.

SUMMARY OF THE DISCLOSURE

A catheter that includes a mechanism for deflecting a distal portion of a catheter is disclosed. The catheter may comprise a deflection knob including a first thread, a rod including a second thread that is coupled to the first thread, and a puller wire that is connected to the rod. The rod may comprise a proximal portion upon which the second thread may be disposed and a distal portion to which the puller wire may be connected. As such, the second thread may be disposed on an outer surface of the rod. In various embodiments, the first thread may comprise an external thread and the second thread may comprise an internal thread. In alternative embodiments, the first thread may comprise an internal thread and the second thread may comprise an external thread.

The distal portion of the rod may include a pocket to which the puller wire may be connected. Specifically, a joining feature may be secured in the pocket and attached to a proximal end of the puller wire. The joining feature may comprise a first ferrule joined, e.g., crimped, to the proximal end of the puller wire. The joining feature may also comprise a second ferrule secured, e.g., bonded, in the pocket and joined, e.g., crimped, to the first ferrule. In preferred embodiments, the first ferrule comprises stainless steel and the second ferrule comprises brass.

The deflection knob preferably includes a longitudinal bore having a surface such that the first thread may be disposed on the surface and such that the proximal portion of the rod may be disposed through the longitudinal bore. The deflection knob and rod may be incorporated as components of a subassembly into a handle of the catheter. The subassembly may additionally include a stationary component, e.g., a collar. A catheter body of the catheter may be connected at a proximal end to the stationary component and connected at a deflectable distal end to a distal end of the puller wire. Additionally, the rod may define therethrough an internal passageway such that additional structures of the catheter (e.g., irrigation tubing, lead wires) may extend through the internal passageway.

The catheter may thus be used according to methods and variations where the distal end of a catheter body of the catheter may be deflected. Such methods may include rotating the deflection knob, translating the rod, and displacing the puller wire. The step of rotating the deflection knob may cause the steps of translating the rod and displacing the puller wire to occur.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Figure 1:
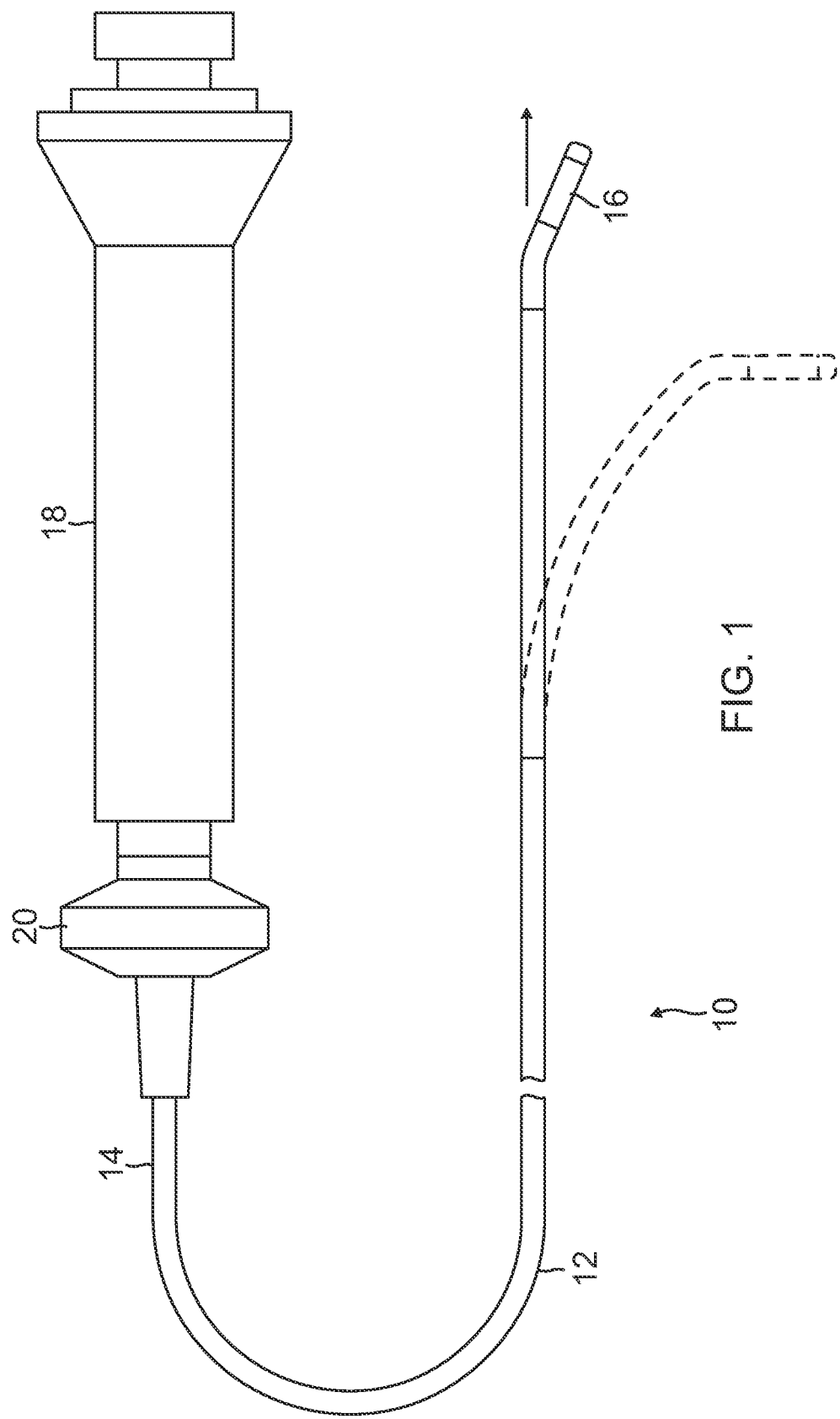
FIG. 1 depicts a catheter having a catheter body and a handle with a deflection knob.
Figure 2:
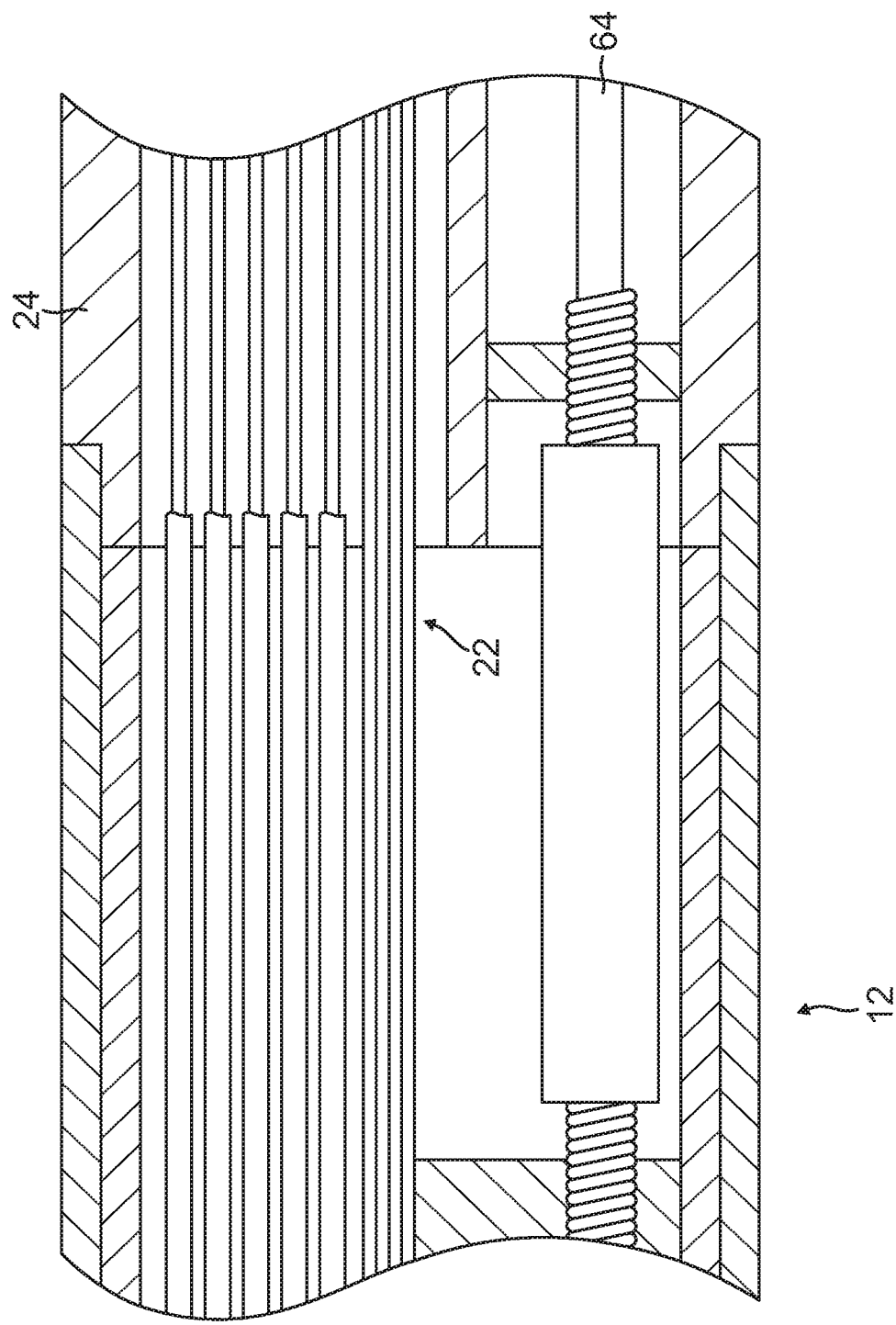
FIG. 2 depicts a cross section of a segment of the catheter body of FIG. 1.

FIG. 1 shows a catheter 10 including an elongated catheter body 12 having proximal and distal ends, 14 and 16, respectively. A control handle 18 including a control knob 20 may be disposed at the proximal end of the catheter body. As seen in FIG. 2, catheter body 12 comprises an elongated tubular construction having an axial or central lumen 22. Catheter body 12 is flexible, i.e., deflectable, but substantially non compressible along its length. Catheter body 12 can be of any suitable construction and made of any suitable material. A presently preferred construction comprises an outer wall 24 made of polyurethane or PEBAX®. The outer wall 24 may comprise an embedded braided mesh of stainless steel or the like to increase torsional stiffness of catheter body 12.

As shown in FIG. 2, a puller wire 64 may be disposed in lumen 22 of catheter body 12. Puller wire 64 is provided for deflection of a portion of the catheter, e.g., the distal end of catheter body 12. As such, the puller wire 64 extends through the catheter body 12 whereupon it may be attached to the distal end of the catheter in lumen 22. A proximal end of puller wire 64 may be anchored to the control handle 18, particularly to a component that may be manipulated via movements of knob 20 as explained below. Puller wire 64 may be fabricated from any suitable metal, such as stainless steel, cobalt chromium, beryllium copper, or Nitinol. Further, it may be coated with a low-friction material, e.g., TEFLON® to impart lubricity to puller wire 64. Puller wire 64 may have a diameter ranging from, e.g., about 0.006 to about 0.010 inch.

Longitudinal movement of the puller wire 64 relative to the catheter body 12, results in deflection of the distal end of catheter body 12. Such movement may be accomplished by suitable manipulation of the control handle 16, as described in, e.g., U.S. Pat. No. Re 34,502 and U.S. Pat. No. 5,897,529, the entire disclosures of which are incorporated herein by reference. Another mechanism for imparting longitudinal movement to puller wire 64 is described with reference to FIGS. 3-6.

Figure 3:
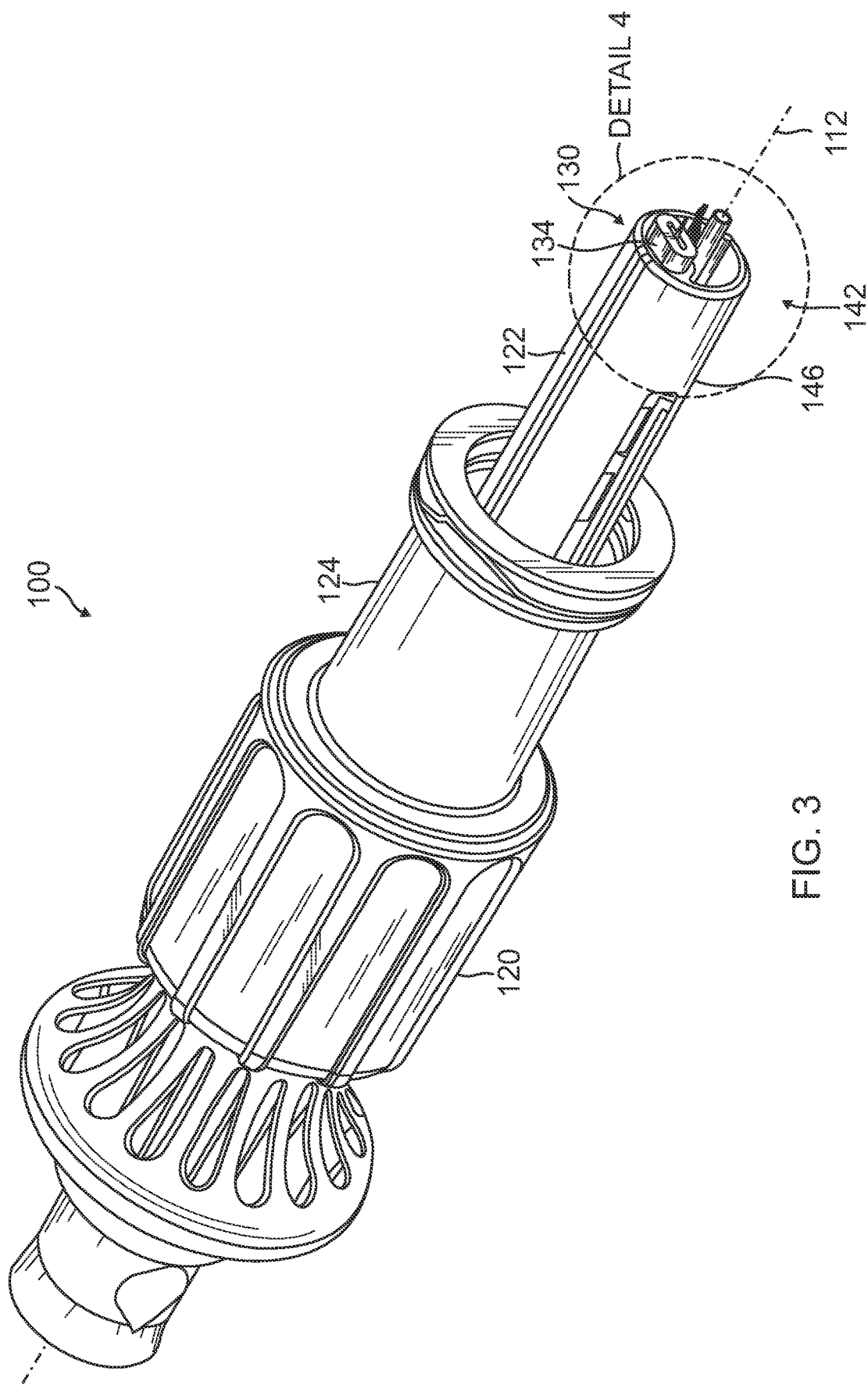
FIG. 3 depicts a perspective view of a subassembly of a catheter handle.

FIG. 3 shows a subassembly 100 of a handle mechanism for use with a deflectable catheter. Subassembly 100 includes a control knob 120, a rod 122, and a stationary component, e.g., collar 124. As shown, knob 120, rod 122, and collar 124 each have a cylindrical form and are arranged concentrically with each other about longitudinal axis 112 of subassembly 100. Such concentricity is not required, however, to practice the disclosed subject matter. Rod 122 may be coupled to control knob 120 such that rotation of knob 120 about axis 112 causes linear motion, i.e., translation of rod 122 relative to knob 120 along or parallel to axis 112. Collar 124 may be maintained in a stationary state relative to knob 120 and rod 122, such that it may be configured to restrict rotational motion of rod 122 about axis 112. As such, rod 122 can be pulled into collar 124 by rotating knob 120 one way (e.g., clockwise) and pushed out of collar 124 by rotating knob 120 the other way (e.g., counterclockwise).

Figure 5:
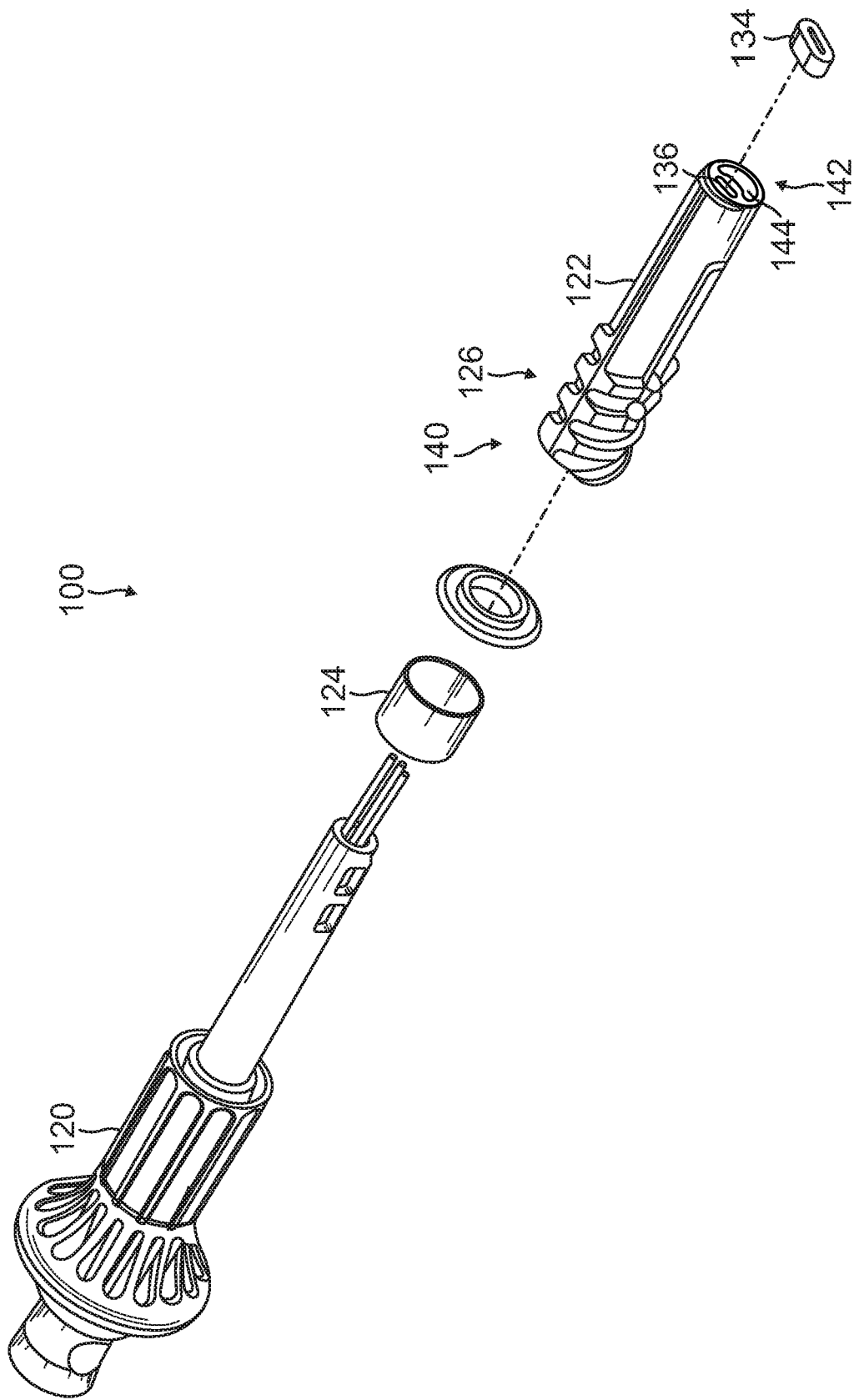
FIG. 5 depicts an exploded view of the subassembly of FIG. 3.
Figure 6:
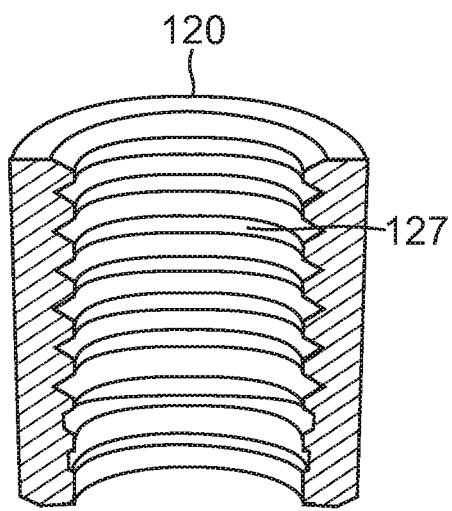
FIG. 6 depicts a section view of a knob component of the subassembly of FIG. 3.

Threads may be used to impart linear motion to rod 122 via application of rotational forces to knob 120. Such a mechanism also prevents linear forces applied to rod 122 from causing knob 120 to rotate. As seen in FIG. 5, which is an exploded view of subassembly 100 with some components removed for clarity, external threads 126 may be disposed on an outer surface 146 of rod 122 at proximal end 140. With further reference to FIG. 6, internal threads 127 may be disposed on an internal surface of knob 120. For example, knob 120 may define a bore therethrough and the internal threads may be disposed about the circumference of the bore. The coupling of knob 120 and rod 122 via their respective threads allow for linear motion of rod 122 to be caused by rotation of knob 120. Of course, the same cause and effect may be realized by providing rod 122 with internal threads and knob 120 with external threads.

Figure 4:
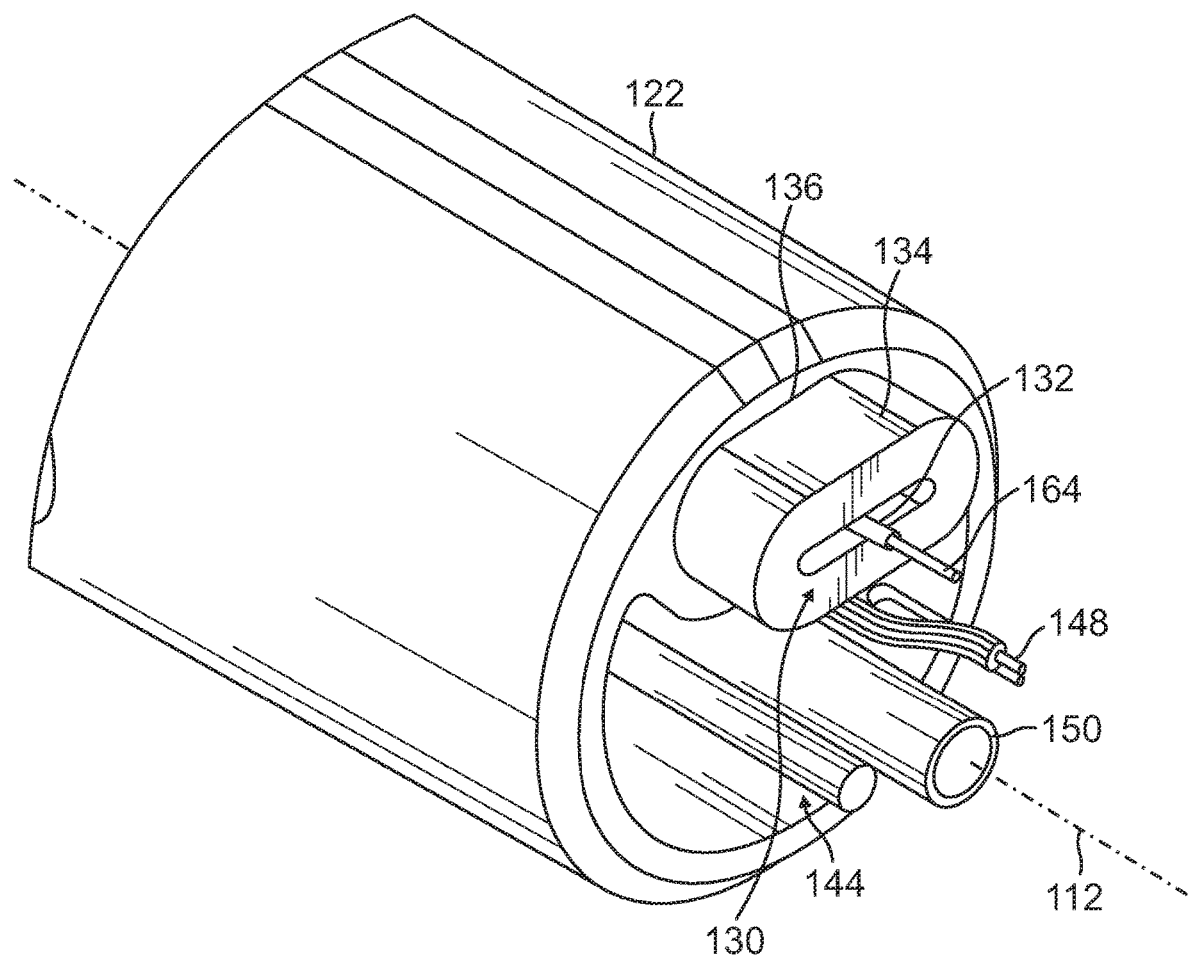
FIG. 4 depicts a detail view of the distal end of the subassembly of FIG. 3 as indicated by the circle labeled "Detail 4" in FIG. 3.

Rod 122 may be connected to a puller wire 164, best seen in FIG. 4, which is a detail view of the distal end 142 of rod 122. The connection may be realized via a joining feature 130 connected to distal end 142. Preferably, joining feature 130 may include between one and three ferrules, e.g., two ferrules. As seen in FIG. 4, a first ferrule 132 may be attached, e.g., crimped, onto puller wire 164, and a second ferrule 134 may be attached, e.g., crimped, onto first ferrule 132. Second ferrule 134 may be coupled to distal end 142 of rod 122 by attaching it thereto via a pocket 136 formed in distal end 142. For example, second ferrule 134 may be bonded or glued in pocket 136. In preferred embodiments, first ferrule 132 may be fabricated from stainless steel and second ferrule 134 may be fabricated from brass. Joining feature 130 provides a robust joint between rod 122 and puller wire 164 because the surface area of second ferrule 134 in pocket 136 is substantially greater than the surface area of a proximal portion of wire 164 that might otherwise be directly attached therein. As such, friction forces and other bonding forces between pocket 136 and second ferrule 134 are greater than they would otherwise be if a proximal portion of wire 164 were directly attached to rod 122 without ferrule 134. First ferrule 132 also contributes to the robustness of the joint. As shown, first ferrule 132 has a cylindrical form, which allows it to be crimped onto the proximal end of wire 164 without pinching it, damaging it, or otherwise causing a stress concentration that could lower the maximum tensile load or number of cycles that wire 164 would otherwise be able to handle until failure.

Because puller wire 164 is connected to rod 122 via joining feature 130, linear motion of rod 122 effected by rotation of knob 120 causes a corresponding linear motion or displacement of puller wire 164. By connecting puller wire 164 to another object, that object may be manipulated by movements of puller wire 164 caused by rotations of knob 120.

A catheter body of a catheter, such as catheter body 12 of catheter 10, may be connected at its proximal end to handle subassembly 100, e.g., directly or indirectly to the stationary component, e.g., collar 124. Preferably, proximal end 14 of catheter body 12 has an internal diameter slightly smaller to slightly larger than the outer diameter of collar 124 to permit attachment via, e.g., an interference fit, bonding with an adhesive, or both. Because rod 122 may be advanced or retracted through collar 124, the outer diameter of rod 122 is smaller than the inner diameter of collar 124, indicating that the outer diameter of rod 122 is also smaller than the inner diameter of catheter body 12. As such, puller wire 164 may extend through catheter body 12, from its proximal end 14 to its distal end 16. Puller wire 164 may further be anchored at the distal end 16 of catheter body 12, e.g., via a glue joint. Accordingly, translating puller wire 164 proximally causes distal end 16 of catheter body 12 to deflect, e.g., toward the dotted line shape shown in FIG. 1. Subsequent distal translation of puller wire 164 causes distal end 16 of catheter 12 to return toward its original shape.

Rod 122 additionally defines an internal passageway 144 therethrough. Additional catheter structures that pass through handle subassembly 100 may pass through passageway 144. For example, lead wires 148 and an irrigation tube 150 may be disposed through passageway 144.

By virtue of the embodiments illustrated and described herein, Applicant has devised a method and variations thereof for using a catheter, such as catheter 10 including subassembly 100, the method including steps of rotating a deflection knob (e.g., knob 120), translating a rod (e.g., rod 122), and displacing a puller wire (e.g., 164). In preferred variations, the step of rotating the deflection knob causes the steps of translating the rod and displacing the puller wire to occur, which causes the distal end of the catheter body to deflect.

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A catheter, comprising:
   a deflection knob including a first thread;
   a rod comprising a proximal portion, a distal portion, and a second thread that is coupled to the first thread; and
   a puller wire that is connected to a pocket disposed in the distal portion of the rod by a joining feature secured in the pocket and attached to a proximal end of the puller wire, the joining feature comprising:
      a first ferrule joined to the proximal end of the puller wire; and
      a second ferrule secured in the pocket and joined to the first ferrule.

2. The catheter of claim 1, in which the second thread is disposed along the proximal portion of the rod.

3. The catheter of claim 2, in which the second thread is disposed on an outer surface of the rod.

4. The catheter of claim 2, in which the first ferrule is crimped onto the proximal end of the puller wire.

5. The catheter of claim 4, in which the second ferrule is crimped onto the first ferrule.

6. The catheter of claim 4, in which the second ferrule is bonded to the pocket.

7. The catheter of claim 4, in which the first thread comprises an internal thread.

8. The catheter of claim 4, in which the second thread comprises an external thread.

9. The catheter of claim 4, in which the deflection knob includes a longitudinal bore having a surface and the first thread is disposed on the surface.

10. The catheter of claim 9, in which a portion of the proximal portion of the rod is disposed through the longitudinal bore.

11. The catheter of claim 10, further comprising a handle including the deflection knob, the rod, and a stationary component.

12. The catheter of claim 11, further comprising a catheter body having a proximal end connected to the stationary component and a deflectable distal end connected to a distal end of the puller wire.

13. The catheter of claim 12, in which the rod defines therethrough an internal passageway and the catheter further comprises a structure extending through the internal passageway.

14. The catheter of claim 13, in which the structure comprises an irrigation tube.

15. The catheter of claim 14, in which the structure comprises a wire.

16. The catheter of claim 4, in which the first ferrule comprises stainless steel.

17. The catheter of claim 16, in which the second ferrule comprises brass.

* * * * *